US012710434B2

(12) United States Patent
Alzona et al.

(10) Patent No.: US 12,710,434 B2
(45) **Date of Patent: *Aug. 18, 2026**

(54) RED CELL DILUENT WITH CHELATING AGENT AND METHODS FOR MAKING AND USING THE SAME

(71) Applicant: Immucor, Inc., Norcross, GA (US)

(72) Inventors: Mortimer Alzona, Norcross, GA (US); Bryan Marshall, Norcross, GA (US); Elizabeth Cope, Norcross, GA (US); Margot Borgel, Norcross, GA (US); Teresa Welch, Norcross, GA (US)

(73) Assignee: Immucor, Inc., Norcross, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,356

(22) Filed: Aug. 4, 2023

(65) Prior Publication Data

US 2023/0375574 A1 Nov. 23, 2023

Related U.S. Application Data

(62) Division of application No. 16/500,713, filed as application No. PCT/US2018/025918 on Apr. 3, 2018, now Pat. No. 11,754,574.

(60) Provisional application No. 62/480,879, filed on Apr. 3, 2017.

(51) Int. Cl.

| | |
|---|---|
| ***G01N 33/80*** | (2006.01) |
| ***G01N 1/38*** | (2006.01) |
| ***G01N 33/50*** | (2006.01) |
| ***G01N 33/68*** | (2006.01) |

(52) U.S. Cl.
CPC ............... *G01N 33/80* (2013.01); *G01N 1/38* (2013.01); *G01N 33/5005* (2013.01); *G01N 33/6854* (2013.01)

(58) Field of Classification Search
CPC ............... G01N 33/80; G01N 33/5005; G01N 33/6854; G01N 1/38; G01N 33/56966
See application file for complete search history.

(56) References Cited

U.S. PATENT DOCUMENTS

| | | | | |
|---|---|---|---|---|
| 6,884,573 B2 * | 4/2005 | Fischer | A01N 1/126 | 424/93.73 |
| 2002/0022271 A1 * | 2/2002 | Ryan | G01N 33/96 | 422/50 |
| 2010/0178656 A1 * | 7/2010 | Buffiere | G01N 33/54333 | 435/7.1 |

(Continued)

OTHER PUBLICATIONS

Banfi et al. The role of ethylenediaminetetraacetic acid (EDTA) as in vitro anticoagulant for diagnostic purposes. Clin. Chem. Lab. Med. 45 (5): 565-576 (2007).*

(Continued)

*Primary Examiner* — Gailene Gabel
(74) *Attorney, Agent, or Firm* — ARENTFOX SCHIFF LLP

(57) ABSTRACT

The present disclosure relates to a RBC solution comprising ethylenediaminetetraacetic acid (EDTA) and methods for making and using the same. The solution can comprise EDTA at a concentration from 3-5 g/L, including 4 g/L. Well plates prepared using the solution can provide a decreased rate of false positive results in automated immunoassays for detecting RBC antibodies in a patient sample.

15 Claims, 3 Drawing Sheets

(56) References Cited

U.S. PATENT DOCUMENTS

2012/0294798 A1 11/2012 Nelson et al.

OTHER PUBLICATIONS

Arias et al. (Jun. 2010) "Red Blood Cell Permeabilization by Hypotonic Treatments, Saponin, and Anticancer Avicins", Biochimica et Biophysica Acta (BBA)—Biomembranes, 1798(6); 1189-1196.
Banfi et al. (2007) "The Role of Ethylenediamine Tetraacetic Acid (EDTA) as in Vitro Anticoagulant for Diagnostic Purposes", Clinical Chemistry and Laboratory Medicine, 45(5):565-576.
Musawi et al. (May 2016) "In Vitro Mean Red Blood Cell vol. Change Induced by Diode Pump Solid State Low-Level Laser of 405 nm", Photomedicine and Laser Surgery, 34(5):211-214.
International Search Report issued in International Application No. PCT/US2018/025918 mailed Jul. 20, 2018, 5 pages.
Hartmann et al. Investigating the Role of Surface Materials and Three Dimensional Architecture on in Vitro Differentiation of Porcine Monocyte-Derived Dendritic Cells. PLOS One 11 (6): e0158503 pp. 1-19 (Jun. 30, 2016).

* cited by examiner

RED CELL DILUENT WITH CHELATING AGENT AND METHODS FOR MAKING AND USING THE SAME

CROSS-REFERENCE TO RELATED APPLICATIONS

This application is a divisional of U.S. patent application Ser. No. 16/500,713, which was filed on Oct. 3, 2019 and which issued as U.S. Pat. No. 11,754,574 on Sep. 12, 2023. U.S. patent application Ser. No. 16/500,713 is a national stage entry of PCT Application No. PCT/US2018/025918, which was filed on Apr. 3, 2018. PCT Application No. PCT/US2018/025918 claims priority to U.S. Provisional Application No. 62/480,879, which was filed on Apr. 3, 2017. This application claims priority to U.S. patent application Ser. No. 16/500,713, PCT Application No. PCT/US2018/025918, and U.S. Provisional Application No. 62/480,879.

FIELD OF THE DISCLOSURE

The present disclosure relates to the use of ethylenediaminetetraacetic acid (EDTA) as a component in a red cell diluent (RCD) for the preparation of capture plates for immunoassays. The present disclosure also relates to assays using such plates.

BACKGROUND OF THE DISCLOSURE

Prior to receiving a transfusion involving RBCs (i.e., human RBCs), a patient must be tested for the presence of antibodies against specific RBC antigens, especially those that may cause unwanted reactions in the recipient. Exemplary immunoassays include a hemagglutination reaction in a microtiter based format, including a solid-phase assay. In such methods, microtiter wells contain fragments of RBCs that have been immobilized to the well surface using a linking agent. The RBC fragments display antigens that serve as the capture component of the assay.

As patient samples are added to the wells, any antibodies present within the sample that have a specificity to the red blood cell antigens which are immobilized on the well surface, bind to those antigens. After a series of washing steps, indicator cells (e.g., antibody-coated RBCs) are then added to the well. Indicator cells bind to any antibodies bound to the well. After incubation, the wells are centrifuged. Any unbound indicator cells centrifuge to the center of the well and form a visible pellet. Bound cells remain bound to the well and prevent the formation of a distinct pellet.

The absence of a distinct pellet is interpreted as a positive result whereas the formation of a pellet is interpreted as a negative result. The pellet size and shape can impact the determination from negative through positive with varying degrees of reactivity.

Such assays can be performed manually or with automated systems. Automated systems increase the speed in performing the immunoassays, but can have unexpected positive reactions with negative samples. Negative samples (i.e., samples absent of red blood cell antibodies) can result in positive or equivocal (undetermined) reactions. Such results can require further testing and unnecessarily searching for an alternate donor. There remains a need for an automated immunoassay with a decreased rate of false positive results.

SUMMARY OF THE DISCLOSURE

The present disclosure relates to a RBC solution comprising ethylenediaminetetraacetic acid (EDTA), for example, disodium EDTA and/or tetrasodium EDTA. Well plates prepared using an EDTA-containing RBC solution can provide a decreased rate of false positive results in automated hemagglutination assays.

Described herein are methods of preparing a RBC solution by providing RBCs and suspending the RBCs in a solution comprising EDTA. The solution can comprise EDTA at a concentration from 3-5 g/L, including 4 g/L.

Also described herein are methods of preparing a well, for example, wells in a 96-well plate. A well can be prepared by providing RBCs; suspending the RBCs in a solution comprising EDTA; providing a well comprising a RBC attachment molecule bound to a surface of the well; applying RBC solution to the well to bind RBCs to the RBC attachment molecule, thereby immobilizing RBCs in the well; treating the well with a RBC lysing agent; and washing the well; and treating the well with a drying solution (e.g., a desiccant), wherein the prepared well comprises RBC fragments, such as RBC membranes and/or RBC stroma. The present disclosure also relates to wells prepared by these methods.

The present disclosure also relates to methods for detecting RBC antibodies by providing the well prepared according to the disclosed methods, contacting the well with a sample comprising RBC antibodies, and detecting RBC antibodies bound to RBC fragments in the well. Also disclosed herein are kits for detecting RBC antibodies that comprise the well prepared according to the disclosed methods.

DETAILED DESCRIPTION

In the manufacture of well-plates for hemagglutination assays, RBCs can be used to form a cell monolayer attached to the well surface. Red blood cells are sourced as whole or packed cell units from donor centers. Units are washed and resuspended in a buffered red cell storage solution (known as red cell diluent, or RCD). When the RBCs are ready to be used for the manufacture of well-plates, the red cells can be resuspended to a specific concentration (as measured by hematocrit) in RCD.

Ethylenediaminetetraacetic acid (EDTA) can be added to the RCD (RCD containing EDTA, "ERCD") prior to plating. The EDTA can be, for example, disodium EDTA and/or tetrasodium EDTA. This dilutes (i.e., bulks) the RBCs prior to plating. Including EDTA in the RCD can result in coated well-plates that have reduced rates of unexpected false positive/equivocal assay results, including in automated assays.

The RBC solutions (i.e., RBCs suspended in RCD) disclosed herein can comprise EDTA in the RCD at a concentration of about 3-5 g/L. For example, EDTA can be included at a concentration of about 3 g/L, at about 4 g/L, or about 5 g/L. The EDTA can be included at 3 g/L, 4 g/L, or 5 g/L. The EDTA can be included at 3.0 g/L, 3.1 g/L, 3.2 g/L, 3.3 g/L, 3.4 g/L, 3.5 g/L, 3.6 g/L, 3.7 g/L, 3.8 g/L, 3.9 g/L, 4.0 g/L, 4.1 g/L, 4.2 g/L, 4.3 g/L, 4.4 g/L, 4.5 g/L, 4.6 g/L, 4.7 g/L, 4.8 g/L, 4.9 g/L, or 5.0 g/L.

Methods of preparing such a RBC solution can comprise providing RBCs and suspending the RBCs in a solution comprising EDTA. The EDTA can be, for example, disodium EDTA and/or tetrasodium EDTA. EDTA can be included in the solution at the above-identified concentrations.

Wells, such as in a microtiter well-plate or a microtiter well-strip, can be prepared by providing or preparing the EDTA-containing RBC solution described herein. An attachment molecule can be incubated in a well so that it adheres to the well surface. After incubation, the well can be washed to remove excess unbound material. Washing can manual or automated. The EDTA-containing RBC solution can be added to the well and allowed to incubate, for example, overnight, to allow adhesion of the RBCs to the well surface, via the attachment molecule.

Figure 3:
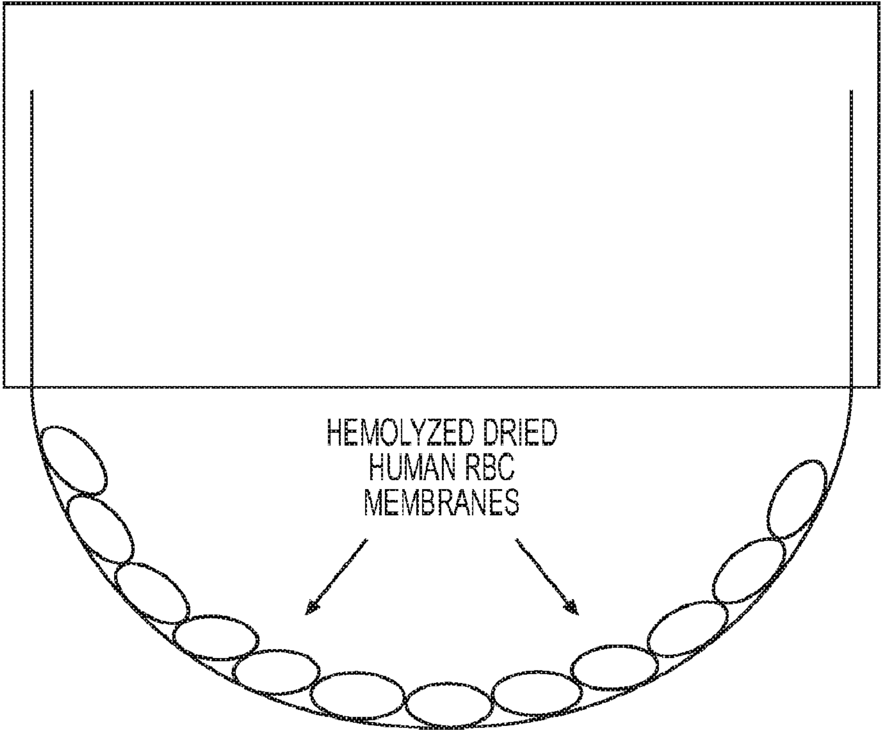
FIG. 3 shows a microtiter well coated with human RBC membranes prepared in accordance with the methods described herein.

Next, a lysing solution can be added to the well to lyse the RBCs. The wells can be washed to remove cellular debris. Only bound cell fragments containing specific antigens, for example, antigens to antibodies whose presence are to be identified in a patient sample, including IgG antibodies, can remain in the well. A drying solution can be added to the wells prior to further packaging or storage. After a curing period, for example, at least or about three days, the well-plate can be stored at ambient temperature. FIG. 3 shows a prepared well.

Wells, well-plates, and/or well-strips prepared in accordance with the methods described herein can be included in a kit for detecting RBC antibodies. The kit can include additional elements required for the assay, such as indicator cells.

Wells or well-plates prepared in accordance with the methods described herein can be used in methods for detecting RBC antibodies, including manual and automated methods. The methods can include steps of providing the wells or well-plates described herein, contacting the well with a sample comprising RBC antibodies, and detecting RBC antibodies bound to RBC fragments in the well. The sample can be a biological sample containing antibodies to RBC antigens, such as a blood, plasma, or serum sample. The biological sample can be treated with other substances, such as anti-coagulants, needed to preserve the sample for the time period between obtaining the sample from a patient and testing the sample. The sample can be obtained from a patient requiring a blood transfusion, for example, a patient who is to be tested for the presence of antibodies, including alloantibodies to RBC antigens.

Figure 1:
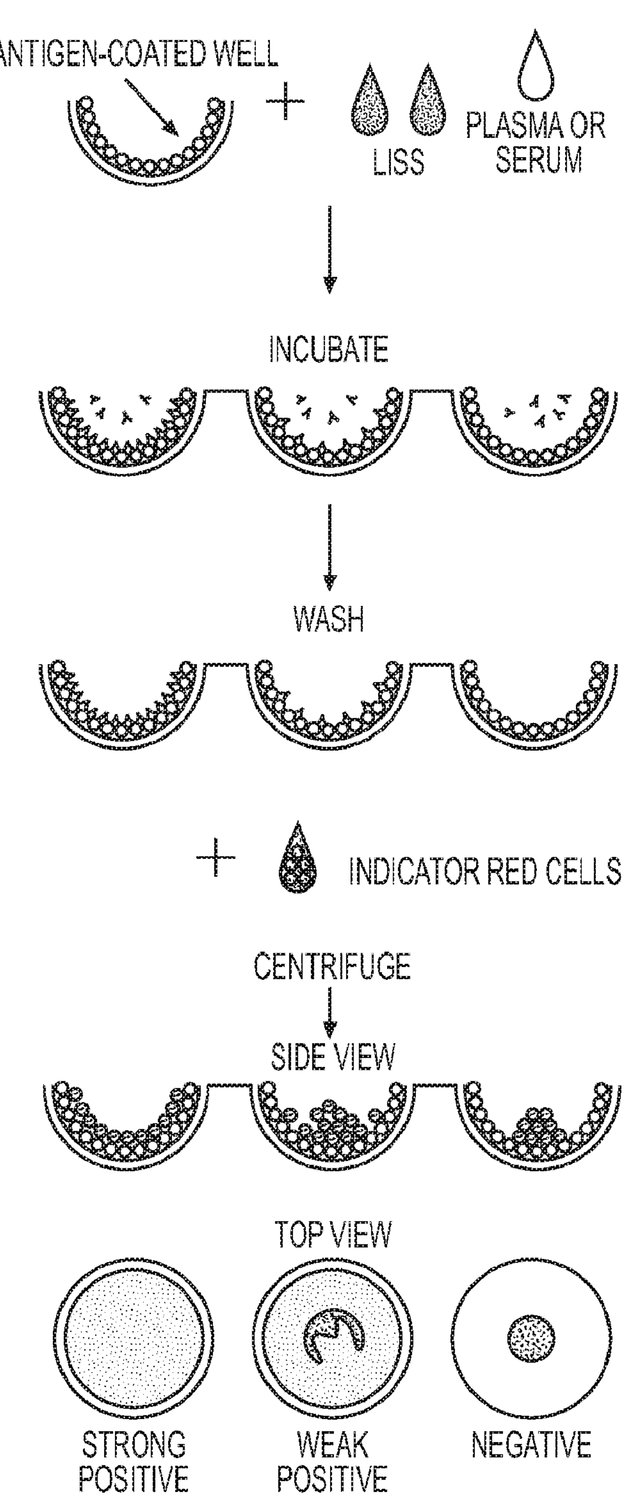
FIG. 1 shows the steps of an immunoassay to detect the presence of RBC antibodies.

FIG. 1 shows exemplary steps of the detection methods. In the detection methods, any antibodies present within the sample that have a specificity to the RBC antigens that are immobilized on the well surface, can bind to those antigens. Such antibodies can include antibodies typically tested in hemagglutination assays. Such antibodies can include IgG antibodies, for example, clinically significant IgG antibodies. Such antibodies can include antibodies associated with hemolytic disease of the newborn. Such antibodies can include Kidd antibodies (including anti-$Jk^a$ and anti-$Jk^b$), Kell antibodies (including anti-K), and/or MNS antibodies (including anti-S).

The antigen-coated well, which is prepared in accordance with the method described above, is provided. To test for RBC antibodies, such as IgG antibodies, a patient plasma or serum sample can added to the well, optionally, with a low ionic strength saline (LISS) solution to increase the amount of antibody taken up by the RBC cells or RBC fragments in the well during subsequent sensitization. An exemplary LISS solution can comprise glycine, bromcresol purple dye and sodium azide as a preservative. After an incubation period, the wells can be washed one or more times to remove unbound antibodies.

Indicator cells can then be added to the wells to detect bound antibodies. The indicator cells can be antibody-coated RBCs, such as RBCs coated with an anti-IgG antibody. The indicator cells can be in the form of a suspension of red blood cells coated with murine monoclonal anti-human IgG molecules. Indicator cells can bind to any antibodies bound to the well (e.g., antibodies bound to the RBC cell monolayer coating the well).

The wells or plate can then be centrifuged. When the wells are then centrifuged, the IgG/Anti-IgG binding will prevent the indicator cells from migrating to the bottom of the well—if antibody was bound during the incubation phase. Any unbound indicator cells can centrifuge to the center of the well and form a visible pellet. Bound cells can remain bound to the well and can prevent the formation of a distinct pellet.

Figure 2:
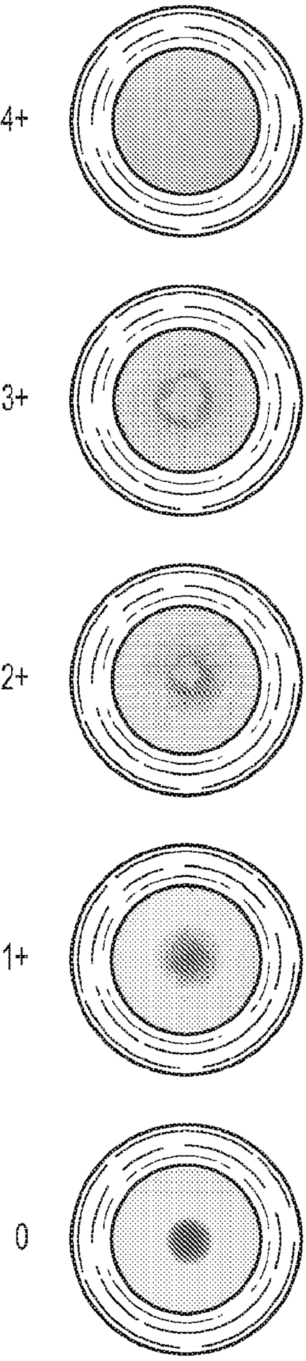
FIG. 2 shows a grading chart for automated RBC antibody detection using wells and plates prepared according to the present disclosure.

Automated detection systems can be used to perform the detection method. The absence of a distinct pellet can be interpreted as a positive result (4+ in FIG. 2) and the formation of a pellet can be interpreted as a negative result (0 in FIG. 2). The pellet size and shape can impact the determination from negative through positive with varying degrees of reactivity (1+ through 3+ in FIG. 2). The rate of unexpected false positive/equivocal assay results can be reduced in such methods. Automated systems and assays can involve machine detection and scoring of hemaaglutination reactions (i.e., pellet/reactivity scoring). Exemplary automated systems include the Echo®, Galileo®, and NEO® systems of Immucor®.

The assays and kits disclosed herein can also use or include positive and negative control reagents. An exemplary positive control reagent can comprise antibodies to red blood cells. An exemplary negative control reagent contains no antibodies to red blood cells.

EXAMPLES

The following examples are offered by way of illustration and not by way of limitation n.

Example 1—Preparation of RBC-EDTA Solutions

Red blood cells are sourced as whole or packed cell units from donor centers. Prior to plating, the units are prepared for plating by washing and resuspending them in a red cell storage solution (red cell diluent, or RCD) that includes disodium EDTA at a concentration of 4 g/L.

Example 2—Preparation of Well Plate 96-well polystyrene plates or 8-well polystyrene strips are added to an automation line where an attachment molecule is added to each well. The attachment molecule is incubated to allow adhesion to the well surface and then excess and unbound material is washed away. RBCs from the solution prepared in Example 1 are then added to each well and allowed to incubate overnight to allow adhesion of the red cells to the well surface (via the attachment molecule).

Subsequent to overnight incubation, a lysing solution is added to each well to lyse the red cells. Wells are washed and cellular debris is removed leaving only the bound cell fragments containing specific red cell antigens. A drying solution is added to the plates and the plates are packaged and stored in a cooler for a minimum of three days to allow further "curing" of the product. The plates are then stored at ambient temperature.

Example 3—Assay

The well-plate or strip of Example 2 can be used in an immunoassay to detect RBC antibodies using automated equipment. A patient plasma sample and LISS are added to the wells in the well-plate. The sample is incubated in the wells so that IgG antibodies present within the sample that have a specificity to the red blood cell antigens that are immobilized on the well surface, bind to those antigens. The wells are washed one or more times.

Indicator cells (RBCS coated with anti-IgG antibody) are added to the well. Indicator cells bind to any antibodies bound to the well. After incubation, the wells are centrifuged. Any unbound indicator cells centrifuge to the center of the well and form a visible pellet. Bound cells remain bound to the well and would prevent the formation of a distinct pellet. The automated equipment determines the results from negative through positive with varying degrees of reactivity. There is a lower rate of false positive rates in the assay using the plates prepared in accordance with Example 2 than with conventional plates.

Example 4—Kit and Assay

A kit is provided comprising the well-plate or strip of Example 2, LISS solution, and indicator red cells. A patient serum or plasma sample is provided. All reagents and the patient sample(s) are brought to 18-30° C. Two drops (100+/−10 uL) of the LISS solution is added to each well. One drop (50±5 uL) of the test serum/plasma is added to each well.

The wells are incubated at 36-38° C. for 15-60 minutes. The sample-LISS mixture is decanted or aspirated from the wells. The wells are washed with saline. One drop (50±5 uL) of indicator red cells are added to each well. The wells are centrifuged for 1-3 minutes at 450-600×g. After centrifugation, the wells are examined for the adherence or the absence of indicator red cell adherence, either manually or using automated equipment, and scored, for example, using the scale shown in FIG. 2.

While the foregoing disclosure provides some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

The invention claimed is:

1. A method comprising:

preparing a red blood cell (RBC) solution comprising RBCs and a chelating agent, the RBCs comprising antigens to antibodies to be identified in a patient sample;

applying the RBC solution to a structure to cause the RBCs in the solution to be adhered to a surface of the structure; and applying a drying solution to the structure having the RBCs or fragments of the RBCs adhered to the surface of the structure.

2. The method of claim 1, wherein the chelating agent comprises ethylenediaminetetraacetic acid (EDTA).

3. The method of claim 2, wherein the RBCs comprise packed RBCs.

4. The method of claim 3, wherein the EDTA comprises one or more of disodium EDTA and tetrasodium EDTA.

5. The method of claim 4, wherein the solution comprises EDTA at a concentration from about 3 g/L (grams per liter) to about 5 g/L.

6. The method of claim 5, wherein the concentration of EDTA is about 4 g/L.

7. The method of claim 1, further comprising:

applying a lysing agent to RBCs adhered to the structure to produce the fragments of the RBCs.

8. The method of claim 7, wherein the RBC fragments comprise at least one of RBC membranes or RBC stroma.

9. The method of claim 1, further comprising, prior to applying the RBC solution:

applying attachment molecules to the structure; and incubating the attachment molecules so that the attachment molecules adhere to the surface of the structure;

wherein the RBCs or the fragments of the RBCs are bound to respective attachment molecules.

10. The method of claim 9, further comprising, after the RBCs or the fragments of the RBCs are bound to respective attachment molecules:

washing the structure, thereby leaving the RBCs or the fragments of the RBCs bound to the respective attachment molecules.

11. The method of claim 1, further comprising:

following application of the drying solution, curing the structure having the RBCs or the fragments of the RBCs adhered to the surface of the structure for a period of time.

12. The method of claim 11, wherein the period of time is at least three days.

13. The method of claim 1, wherein the structure comprises a well, a plate, or a strip.

14. The method of claim 1, further comprising:

incorporating the structure having the RBCs or the fragments of the RBCs adhered to the surface thereof into a kit.

15. The method of claim 14, wherein the kit comprises:

low ionic strength saline (LISS) solution; and indicator cells coated with anti-IgG antibody.

* * * * *